(12) United States Patent
Ahmad et al.

(10) Patent No.: US 10,258,246 B2
(45) Date of Patent: Apr. 16, 2019

(54) DIRECT INVERSION FOR PHASE-BASED DYNAMIC MAGNETIC RESONANCE MEASUREMENTS

(71) Applicant: Ohio State Innovation Foundation, Columbus, OH (US)

(72) Inventors: Rizwan Ahmad, Columbus, OH (US); Orlando P. Simonetti, Columbus, OH (US); Yu Ding, Hilliard, OH (US); Ning Jin, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 1163 days.

(21) Appl. No.: 14/258,268

(22) Filed: Apr. 22, 2014

(65) Prior Publication Data

US 2014/0316250 A1 Oct. 23, 2014

Related U.S. Application Data

(60) Provisional application No. 61/814,506, filed on Apr. 22, 2013.

(51) Int. Cl.
*A61B 5/00* (2006.01)
*A61B 5/026* (2006.01)
(Continued)

(52) U.S. Cl.
CPC .......... *A61B 5/0263* (2013.01); *A61B 5/055* (2013.01); *A61B 5/7203* (2013.01);
(Continued)

(58) Field of Classification Search
CPC ... A61B 2576/00; A61B 5/0263; A61B 5/055; A61B 5/7203; A61B 5/7239;
(Continued)

(56) References Cited

U.S. PATENT DOCUMENTS

| 2005/0270024 A1* | 12/2005 | Lin | ................... G01R 33/5611 |
| | | | 324/307 |
| 2011/0044524 A1* | 2/2011 | Wang | ................... G01R 33/54 |
| | | | 382/131 |

(Continued)

OTHER PUBLICATIONS

Bostan et al. "Spatio-Temporal Regularization of Flow-Fields." 2013 IEEE 10th International Symposium on Biomedical Imaging: From Nano to Macro. Apr. 2013.*

(Continued)

*Primary Examiner* — Amanda Lauritzen Moher
(74) *Attorney, Agent, or Firm* — Meunier Carlin & Curfman LLC (57) ABSTRACT

MRI techniques seek to simultaneously measure physiological parameters in multiple directions, requiring the application of multiple encoding magnetic field gradient waveforms. The use of multiple encoding waveforms degrades the temporal resolution of the measurement, or may distort the results depending on the methodology used to derive physiological parameters from the measured data. The disclosed Direct Inversion Reconstruction Method (DiR) provides distortion-free velocity images with high temporal resolution, without changing the method of acquiring the phase data. The disclosed method provides a more stable and accurate recovery of phase-based dynamic magnetic resonance signals with higher temporal resolution than current state-of-the-art methods.

11 Claims, 5 Drawing Sheets

(51) Int. Cl.

| | |
|---|---|
| *G01R 33/56* | (2006.01) |
| *G01R 33/44* | (2006.01) |
| *G01R 33/48* | (2006.01) |
| *G01R 33/20* | (2006.01) |
| *G01R 33/00* | (2006.01) |
| *G06T 11/00* | (2006.01) |
| *G01R 33/563* | (2006.01) |
| *A61B 5/055* | (2006.01) |
| *G01R 33/54* | (2006.01) |
| *A61B 6/00* | (2006.01) |

(52) U.S. Cl.
CPC ............ *A61B 5/7239* (2013.01); *G01R 33/00* (2013.01); *G01R 33/20* (2013.01); *G01R 33/44* (2013.01); *G01R 33/48* (2013.01); *G01R 33/56* (2013.01); *G01R 33/56316* (2013.01); *G06T 11/005* (2013.01); *A61B 6/504* (2013.01); *A61B 2576/00* (2013.01); *G01R 33/482* (2013.01); *G01R 33/54* (2013.01); *G01R 33/56308* (2013.01)

(58) Field of Classification Search
CPC .. A61B 6/504; G01R 33/56316; G01R 33/00; G01R 33/56; G01R 33/20; G01R 33/44; G01R 33/48; G01R 33/482; G01R 33/54; G01R 33/56308; G06T 11/005
See application file for complete search history.

(56) References Cited

U.S. PATENT DOCUMENTS

| | | | | |
|---|---|---|---|---|
| 2013/0181711 | A1* | 7/2013 | Chaari | G01R 33/5611 324/309 |
| 2013/0279786 | A1* | 10/2013 | Lin | G06T 11/005 382/131 |

OTHER PUBLICATIONS

Benning et al. "Phase Reconstruction from Velocity-Encoded MRI Measurements—A survey of Sparsity-Promotion Variational Approaches." Oct. 2013.*

Pelc et al. "Encoding Strategies for Three-Direction Phase-Contrast MR Imaging of Flow." Journal of Magnetic Resonance Imaging 1(4). Jul. 1991.*

Bender, J. A., Ahmad, R., & Simonelli, O. P. (2013). The importance of k-space trajectory on off-resonance artifact in segmented echo-planar imaging. Concepts in Magnetic Resonance Part A, 42(2), 23-31.

Breuer, F. A., Kellman, P., Griswold, M. A., & Jakob, P. M. (2005). Dynamic autocalibrated parallel imaging using temporal GRAPPA (TGRAPPA). Magnetic resonance in medicine, 53(4), 981-985.

Hausmann, R., Lewin, J. S., & Laub, G. (1991). Phase-contrast MR angiography with reduced acquisition time: New concepts in sequence design. Journal of Magnetic Resonance Imaging, 1(4), 415-422.

Johnson, K. M., & Markl, M. (2010). Improved SNR in phase contrast velocimetry with five-point balanced flow encoding. Magnetic resonance in medicine, 63(2), 349-355.

Lotz, J., Meier, C., Leppert, A., & Galanski, M. (2002). Cardiovascular Flow Measurement with Phase-Contrast MR Imaging: Basic Facts and Implementation 1. Radiographics, 22(3), 651-671.

Pelc, N. J., Bernstein, M. A., Shimakawa, A., & Glover, G. H. (1991). Encoding strategies for three-direction phase-contrast MR imaging of flow. Journal of Magnetic Resonance Imaging, 1(4), 405-413.

Santini et al. (2009). On optimal encoding of flow in three-dimensional phase-contrast sequences. Proc. International Soc. Mag. Reson. Med., 17, 4537.

Sørensen et al. (2005). Three-dimensional, isotropic MRI: a unified approach to quantification and visualization in congenital heart disease. The International Journal of Cardiovascular Imaging, 21, 283-292.

Zhong, X. Helm, P. A., & Epstein, F. H. (2009). Balanced multipoint displacement encoding for DENSE MRI. Magnetic resonance in medicine, 61(4), 981-988.

* cited by examiner

DIRECT INVERSION FOR PHASE-BASED DYNAMIC MAGNETIC RESONANCE MEASUREMENTS

CROSS-REFERENCE TO RELATED APPLICATION

The present application claims priority to U.S. Provisional Patent Application No. 61/814,506, filed Apr. 22, 2013, entitled "Direction Inversion for Phase-Based Dynamic Magnetic Resonance Measurements," the disclosure of which is incorporated by reference in its entirety.

STATEMENT OF GOVERNMENT SUPPORT

This invention was made with government support under R01 HL102450 awarded by the National Institutes of Health. The government has certain rights in the invention.

BACKGROUND

Phase contrast cardiac magnetic resonance imaging (PC-MRI) is widely used for the clinical in-vivo assessment of blood flow in the diagnosing of various diseases and the depiction of the vessels in the body. Through-plane aortic and pulmonic blood flow are measured and used for the evaluation of cardiac function and output, mitral regurgitation, and shunts. Clinically, a through-plane 2D image acquisition is performed for the evaluation of blood flow. 3D time-resolved PC image processing may be performed that allows quantification and visualization of the blood flow in all three directions. However, lengthy acquisition times have prevented the multi-directional PC techniques from coming into widespread usage.

A balanced four-point encoding (BFPE) is a commonly used encoding strategy for three-directional PC-MRI. In BFPE, each reconstructed frame corresponds to one of the four encodings. To save acquisition time, traditionally, four adjacent frames are processed together on a pixel-by-pixel basis to estimate the unknown phase (velocity). The processing is done by taking the four adjacent (in time) measurements and solving a set of 4×4 equations. If $m_{1:4}$ represent the first four measurements, and $E_{1:4}$ the first four encoding directions, $\vec{\phi}_1$ can be obtained by solving the equations.

$$E_{1:4}\vec{\phi}_1 = m_{1:4}$$

The window is moved by a step of 4 and the process is repeated for the next four measurements.

$$E_{5:8}\vec{\phi}_5 = m_{5:8}$$

To improve temporal resolution, the sliding window approach is often used where the window is advanced by a step of one instead of four frames at a time. It allows reconstructing phase (velocity) at a temporal grid which is four times finer.

$$E_{1:4}\vec{\phi}_1 = m_{1:4}$$

$$E_{2:4}\vec{\phi}_2 = m_{2:5}$$

Although the standard sliding window approach may improve the apparent resolution, it often introduces strong oscillatory artifacts because the underlying assumption that the velocities do not change significantly during the timespan of four consecutive measurements is not always valid.

SUMMARY

Disclosed herein are systems and methods for providing a Direct Inversion Reconstruction (DiR) of MRI measurements that provides distortion-free velocity images with high temporal resolution, without changing the method of acquiring the phase data. The disclosed method provides a more stable and accurate recovery of phase-based dynamic magnetic resonance signals with higher temporal resolution than current state-of-the-art methods.

In accordance with an aspect of the invention, a method and MRI apparatus is disclosed that performs a reconstruction of a magnetic resonance imaging (MRI) data set. The method may include reading an image phase ($\vec{\theta}$) along a temporal dimension at pixel or voxel (m); reconstructing an encoding matrix (B), based on the entire velocity encoding sequence used to acquire the MRI data set; constructing a penalty term R to exploit the structure in the temporal direction; and estimating a velocity encoding phase ($\vec{\phi}$) via regularized least squares. For all m, the method may include repeating estimating a phase ($\vec{\phi}$); converting the estimated phase $\vec{\phi}$ to velocity; and creating a spatial and temporal velocity map.

In accordance with aspects of the disclosure estimating the phase is performed using a relationship $\vec{\phi}_{DiR} = \mathrm{argmin}_\phi \| \vec{\theta} - B\vec{\phi}\|_2^2 + \lambda \|R\vec{\phi}\|_p^p$. In this relationship, $\vec{\theta}$ represents all N noisy measurements across time, B is an N×4N underdetermined matrix that represents a forward model, R is the regularization operator, $\lambda$ controls an extent of regularization, $0 \leq p \leq 2$ defines the norm, and $\vec{\phi}_{DiR}$ is a 4N×1 vector that represents an estimate of a true unknown phase $\phi$.

In accordance with aspects of the disclosure estimating the phase is performed using an adaptive relationship $\vec{\phi}_{DiRa} = \mathrm{argmin}_{\lambda_b,\lambda_x,\lambda_y,\lambda_z,\phi} \|\vec{\theta} - B\vec{\phi}\|_2^2 + \lambda_b \|R_b \vec{\phi}\|_p^p + \alpha_x \|R_x \vec{\phi}\|_p^p + \lambda_y \|R_y \vec{\phi}\|_p^p + \lambda_z \|R_z \vec{\phi}\|_p^p$, subject to $1/\lambda_b^\alpha + 1/\lambda_x^\alpha + 1/\lambda_y^\alpha + 1/\lambda_z^\alpha = \mathrm{constant}$. In this adaptive relationship, the values $\lambda_b$, $\lambda_x$, $\lambda_y$, and $\lambda_z$ control the extent of regularization for background, x, y, and z components of an unknown phase, respectively; a user defined constant controls the net regularization strength; $\alpha > 0$ determines the ratio between $\lambda_b$, $\lambda_x$, $\lambda_y$, and $\lambda_z$; $R_*$ is a linear operator that indicates that the regularization is acting only on the "*" component.

Other systems, methods, features and/or advantages will be or may become apparent to one with skilled in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. While implementations will be described for remotely accessing applications, it will become evident to those skilled in the art that the implementations are not limited thereto, but are applicable for remotely accessing any type of data or service via a remote device.

Overview

In cardiovascular diagnostics, the ability to measure blood flow velocity, tissue displacement, and tissue stiffness all carry significant clinical relevance. Magnetic Resonance Imaging (MRI) techniques designed to measure these parameters share some common aspects. For example, the parameter of interest is encoded into the phase of the MRI signal. There are numerous factors that can influence the phase of the MRI signal; thus it is necessary to make multiple measurements and use techniques to remove the effects of extraneous sources of phase. Also, the parameter of interest has a spatial orientation and therefore it is often important to encode and measure components in multiple spatial directions (e.g., x, y, and z). The parameter of interest is dynamically changing and therefore it is important to encode and measure at multiple time points and with high temporal frequency.

These measurements are often made using the electrocardiogram (ECG) signal to synchronize the acquisition of MRI data to the contraction cycle of the heart. This yields a series of image frames spanning the cardiac cycle with each providing anatomical and phase information. The phase information corresponds to the velocity, displacement, or stiffness. For each frame, the encoding can be applied and measurements made in one or multiple directions. The resulting measurements, therefore, may include information in multiple directions and at multiple time points.

MRI techniques seek to simultaneously measure physiological parameters in multiple directions, requiring the application of multiple encoding magnetic field gradient waveforms. The use of multiple encoding waveforms degrades the temporal resolution of the measurement, or may distort the results depending on the methodology used to derive physiological parameters from the measured data.

Herein, is disclosed a Direct Inversion Reconstruction Method (DiR) that provides distortion-free velocity images with high temporal resolution, without changing the method of acquiring the phase data. The disclosed method provides a more stable and accurate recovery of phase-based dynamic magnetic resonance signals with higher temporal resolution than current state-of-the-art methods. It also avoids distortions associated with conventional methods such as the Balanced Four-Point Method.

Example Environment

Figure 1:
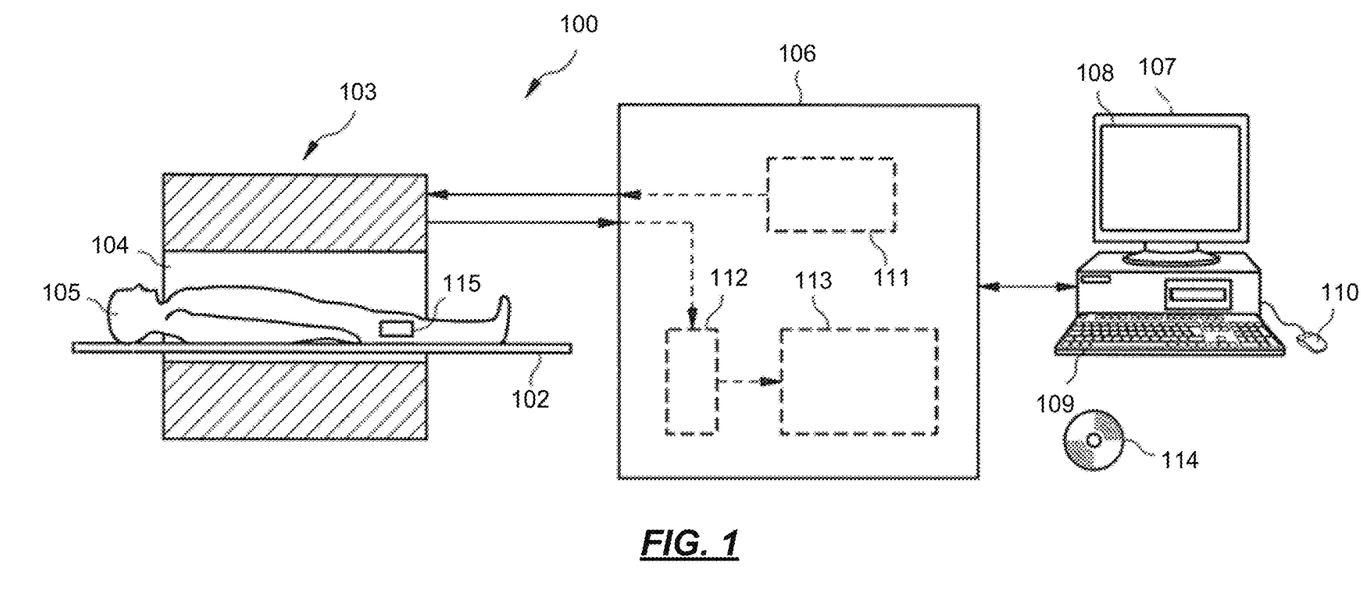
FIG. 1 is a diagram of a structure of a magnetic resonance imaging (MRI) apparatus according to an exemplary embodiment of the present invention.

FIG. 1 is a view illustrating a structure of an example magnetic resonance imaging (MRI) apparatus 100 that may be used to acquire image data. The MRI apparatus 100 includes a scanner 103 that generates magnetic fields used for the MR examination within a measurement space 104 having a patient table 102. A controller 106 includes an activation unit 111, a receiver device 112 and an evaluation module 113. During a phase-sensitive flow measurement, MR data are recorded by the receiver device 112, such that MR data are acquired in, e.g., a measurement volume or region 115 that is located inside the body of a patient 105.

An evaluation module 113 prepares the MR data such that they can be graphically presented on a monitor 108 of a computing device 107 and such that images can be displayed. In addition to the graphical presentation of the MR data, a three-dimensional volume segment to be measured can be identified by a user using the computing device 107. The computing device may include a keyboard 109 and a mouse 110.

Software for the controller 106 may be loaded into the controller 106 using the computing device 107. Such software may implement a method(s) to process data acquired by the MRI apparatus 100, as described below. It is also possible the computing device 107 to operate such software. Yet further, the software implementing the method(s) of the disclosure may be distributed on removable media 114 so that the software can be read from the removable media 14 by the computing device 107 and be copied either into the controller 106 or operated on the computing device 107 itself.

In an implementation, the data acquired by the MRI apparatus 100 of FIG. 1, may be processed as described below with reference to FIGS. 2-7.

Data Modeling

In accordance with the method of direct inversion for phase-based dynamic magnetic resonance measurements of the present disclosure, to encode blood flow using MRI, velocity encoding gradients are applied, which cause a phase evolution of moving spins in proportion to the velocity. In MRI velocity encoding, signal from a given voxel at a given time (j) can be written as $$S^{(j)} = \rho e^{i\gamma \langle \vec{v}^{(j)}, \vec{M}_1^{(j)} \rangle + \phi_b^{(j)}} \quad (1)$$

where $\gamma$ is the gyromagnetic ratio, $\rho$ is the signal intensity or magnitude, superscript $j=1, 2, 3 \ldots N$ indicate time steps at which measurements are taken, $\vec{v}^{(j)} = (v_x^{(j)}, v_y^{(j)}, v_z^{(j)})^T$ is the 3×1 velocity vector, $\vec{M}_1^{(j)} = (M_{1,x}^{(j)}, M_{1,y}^{(j)}, M_{1,z}^{(j)})^T$ is a 3×1 vector of first moments of the applied gradients at echo time, $\phi_b^{(j)}$ is the background (or offset) phase, and $\langle \cdot, \cdot \rangle$ denotes the inner product. Equation 1 can be further simplified to $$S^{(j)} = \rho e^{i \langle \vec{\phi}^{(j)}, \vec{a}^{(j)} \rangle} \quad (2)$$

where $\vec{a}^{(j)} = (a_b^{(j)}, a_x^{(j)}, a_y^{(j)}, a_z^{(j)})^T$ and $\vec{\phi}^{(j)} = (\phi_b^{(j)}, \phi_x^{(j)}, \phi_y^{(j)}, \phi_z^{(j)})^T$, and $\phi_b^{(j)} = 1$, $\phi_x^{(j)} = \gamma v_x^{(j)} M_{1,x}^{(j)}$, $\phi_y^{(j)} = \gamma v_y^{(j)} M_{1,y}^{(j)}$, and $\phi_z^{(j)} = \gamma v_z^{(j)} M_{1,z}^{(j)}$.

Let $\theta^{(j)}$ be the phase of $S^{(j)}$, then:

$$\theta^{(j)} = \langle \vec{\phi}^{(j)}, \vec{a}^{(j)} \rangle \quad (3)$$

where $\theta$ represents all N noisy measurements across time. For given encoding ($\vec{a}^{(j)}$), the velocity measurement is equivalent to estimating $\vec{\phi}^{(j)}$ from noisy measurements ($\theta^{(j)}$).

Conventional Methods

Since each measurement introduces four new unknowns, Equation 3 cannot be solved on measurement-by-measurement basis. Therefore, conventional methods repeat the measurement process multiple times with at least four distinct encoding vectors ($\vec{a}^{(j)}$), yielding:

$$\theta^{(j)} = \langle \vec{\phi}^{(j)}, \vec{a}^{(j)} \rangle$$

$$\theta^{(j+1)} = \langle \vec{\phi}^{(j+1)}, \vec{a}^{(j+1)} \rangle$$

$$\theta^{(j+2)} = \langle \vec{\phi}^{(j+2)}, \vec{a}^{(j+2)} \rangle$$

$$\theta^{(j+3)} = \langle \vec{\phi}^{(j+3)}, \vec{a}^{(j+3)} \rangle. \tag{4}$$

Under the assumption that $\vec{\phi}^{(j)}$ does not change significantly from time j to j+3, Equation 4 can be approximated by:

$$\underbrace{\begin{pmatrix} \theta^{(j)} \\ \theta^{(j+1)} \\ \theta^{(j+2)} \\ \theta^{(j+3)} \end{pmatrix}}_{\vec{\theta}^{(j)}} \approx \underbrace{\begin{pmatrix} \vec{a}^{T(j)} \\ \vec{a}^{T(j+1)} \\ \vec{a}^{T(j+2)} \\ \vec{a}^{T(j+3)} \end{pmatrix}}_{A^{(j)}} \underbrace{\begin{pmatrix} \phi_b^{(j)} \\ \phi_x^{(j)} \\ \phi_y^{(j)} \\ \phi_z^{(j)} \end{pmatrix}}_{\vec{\phi}^{(j)}} = \begin{pmatrix} a_b^{(j)} & a_x^{(j)} & a_y^{(j)} & a_z^{(j)} \\ a_b^{(j+1)} & a_x^{(j+1)} & a_y^{(j+1)} & a_z^{(j+1)} \\ a_b^{(j+2)} & a_x^{(j+2)} & a_y^{(j+2)} & a_z^{(j+2)} \\ a_b^{(j+3)} & a_x^{(j+3)} & a_y^{(j+3)} & a_z^{(j+3)} \end{pmatrix} \begin{pmatrix} \phi_b^{(j)} \\ \phi_x^{(j)} \\ \phi_y^{(j)} \\ \phi_z^{(j)} \end{pmatrix}, \tag{5}$$

which can be efficiently solved by:

$$\vec{\hat{\phi}}^{(j)} = (A^{(j)})^+ \vec{\theta}^{(j)}. \tag{6}$$

Here, $(\cdot)^+$ indicates Moore-Penrose pseudoinverse and $\vec{\hat{\phi}}^{(j)}$ is the estimation of true $\vec{\phi}^{(j)}$.

A most common choice of $A^{(j)}$ is based on balanced four-point acquisition (BFPA), which can be represented by four mutually equidistant points (forming a regular tetrahedron) in $\vec{M}_1$ space. For BFPA, $A^{(1)}$ is given by $$A^{(1)} = \begin{pmatrix} \vec{a}^{T(1)} \\ \vec{a}^{T(2)} \\ \vec{a}^{T(3)} \\ \vec{a}^{T(4)} \end{pmatrix} = \begin{pmatrix} +1 & -1 & -1 & -1 \\ +1 & +1 & +1 & -1 \\ +1 & +1 & -1 & +1 \\ +1 & -1 & +1 & +1 \end{pmatrix}. \tag{7}$$

Here, only four unique encoding vectors are required, and the four step encoding process is repeated in a circular fashion such that every $\vec{a}^{(j+4)} = \vec{a}^{(j)}$ for all j.

Since the MRI data are collected in k-space, reconstruction of MRI images (with two or three spatial and one temporal dimensions) precedes the velocity estimation. From the reconstructed images, the estimation of velocity (phase) is performed on a pixel-by-pixel basis using Equation 6, generating a 2D (or 3D) spatial, 1D temporal map of velocities.

Direct Inversion/Reconstruction Method (DiR)

The conventional BFPA-based (or similar) methods assume $\vec{\phi}^{(j)}$ (or underlying velocity) does not change in the span of four consecutive measurements and only yield approximate solutions when this condition is not met. This approximation often leads to reconstruction artifacts and loss in temporal resolution. On the other hand, the DiR method of the present disclosure is based on direct reconstruction in which all measurements across time are jointly processed. The process is repeated for all pixels (or voxels).

In this method, each measurement is correctly assumed to be taken at a unique time instance. This is a departure from the conventional method where only four (or more) consecutive measurements across time are processed together and treated as if they were acquired simultaneously. In matrix form, Equation 4 becomes $$\begin{pmatrix} \theta^{(1)} \\ \theta^{(2)} \\ \theta^{(3)} \\ \vdots \\ \theta^{(N)} \end{pmatrix}_{\vec{\theta}} = \underbrace{\begin{pmatrix} \vec{a}^{T(1)} & \vec{0} & \vec{0} & \vec{0} & \cdots & \vec{0} \\ \vec{0} & \vec{a}^{T(2)} & \vec{0} & \vec{0} & & \vec{0} \\ \vec{0} & \vec{0} & \vec{a}^{T(3)} & \vec{0} & & \vec{0} \\ \vdots & & & \ddots & & \\ \vec{0} & & & & & \vec{a}^{T(N)} \end{pmatrix}}_{B} \begin{pmatrix} \vec{\phi}^{T(1)} \\ \vec{\phi}^{T(2)} \\ \vdots \\ \vec{\phi}^{T(N)} \end{pmatrix}_{\vec{\phi}}, \tag{8}$$

where $\vec{0} = (0, 0, 0, 0)$. Equation 8 can be equivalently written as:

$$\vec{\theta} = B\vec{\phi} \tag{9}$$

The encoding matrix B is N×4N and does not have an inverse. Also, the minimum norm solution ($\vec{\hat{\phi}} = (B)^+ \vec{\theta}$) generates results with severe oscillations and excessively underestimates the true peak-velocity values.

Instead of finding a least-squares solution or minimum norm solution, in the proposed approach, a regularized least-squares solution to Equation 9 may be used, which can be written as $$\hat{\vec{\phi}} = \underset{\vec{\phi}}{\operatorname{argmin}} \|\vec{\theta} - B\vec{\phi}\|_2^2 + \lambda \|R\vec{\phi}\|_{p'}^p \tag{10}$$

where R is a regularization operator and λ controls the extent of regularization. Reasonable choices of R include finite difference approximations to first-order and second-order temporal derivatives. For 0≤p≤1, other sparsifying transforms can be used for R. For the first-order derivative, the matrix R can be written as $$R = \begin{pmatrix} c & 0 & 0 & 0 & c' & 0 & 0 & 0 & \cdots & 0 \\ 0 & k & 0 & 0 & 0 & k' & 0 & 0 & \cdots & 0 \\ 0 & 0 & k & 0 & 0 & 0 & k' & 0 & \cdots & 0 \\ 0 & 0 & 0 & k & 0 & 0 & 0 & k' & 0 & \cdots & 0 \\ 0 & 0 & 0 & 0 & c & 0 & 0 & 0 & c' & \cdots & 0 \\ & & & & & \vdots & & & & \\ & & & & & \vdots & & & & \\ 0 & \cdots & 0 & 0 & 0 & 0 & k & 0 & 0 & 0 & k' \end{pmatrix} \tag{11}$$

where R is 4(N−1)×4N matrix, c>0 and k>0 are real positive numbers, and $c' = -c$ and $k' = -k$. The constant c appears in every $(4(i-1)+1)^{th}$ row, for i=1, 2, ... N−1, and k appears in all other rows. Since the background phase ($\phi_b$) varies more gradually with time, the roughness in background phase may be penalized by selecting c>k.

For p=2, Equation 10 has a closed form solution, given by $$\vec{\phi}_{DiR} = (B^T B + \lambda R^T R)^{-1} B^T \vec{\theta} \quad (12)$$

The estimation of phase (velocity) using Equation 12 is repeated for all pixels, generating a 2D (or 3D) spatial, 1D temporal map of velocities. For 0≤p≤1, other iterative methods, can be used to solve the regularized least squares problem.

Figure 2:
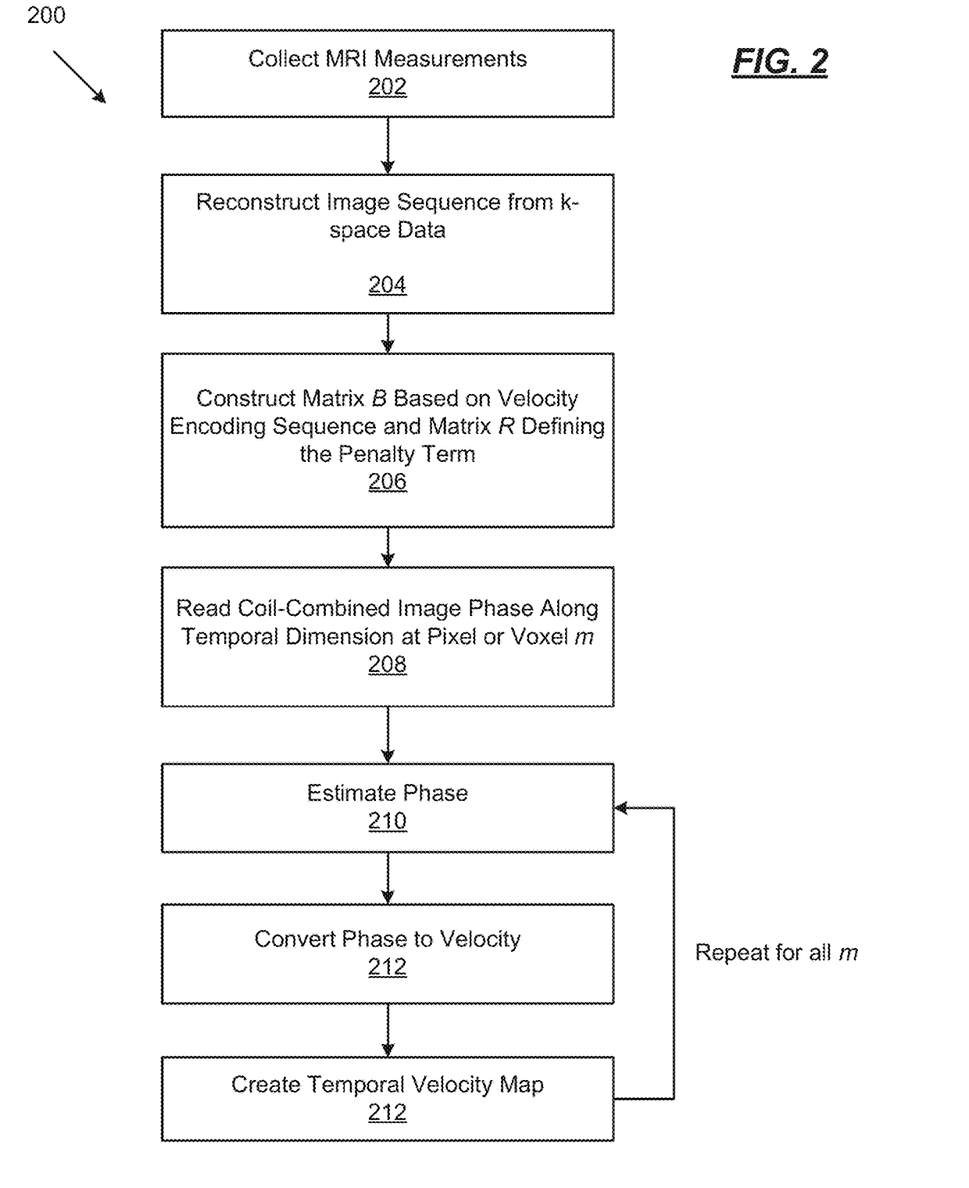
FIG. 2 is an example operational flow in accordance with the present disclosure for implementing a direct inversion reconstruction (DiR) of MRI measurements.

FIG. 2 illustrates an example operational flow 200 in accordance with the present disclosure. At 202, MRI measurements are collected using a balanced four-point acquisition (BFPA) protocol. Other acquisition protocols can also be used. At 204, a 2D (or 3D) spatial, 1D temporal image sequence is reconstructed from the collected k-space data. For example, parallel MRI acquisition and reconstruction methods may be employed to accelerate the acquisition process. At 206, a matrix B is reconstructed based on the velocity encoding ($\vec{a}$) sequence used and a matrix R is constructed based on the selected regularizer. At 208, a coil-combined image phase ($\vec{\theta}$) is read along the temporal dimension at pixel (or voxel) m. At 210, a phase ($\vec{\phi}$) is estimated using Equation 12 or using iterative methods for 0≤p≤1. At 212, based on the values of phase encoding gradient, the estimated phase $\vec{\phi}$ is converted to velocity. At 214, a 2D (or 3D) spatial, 1D temporal velocity map is created. Steps 210-214 are repeated for all m.

Simulation Results

Figure 3:
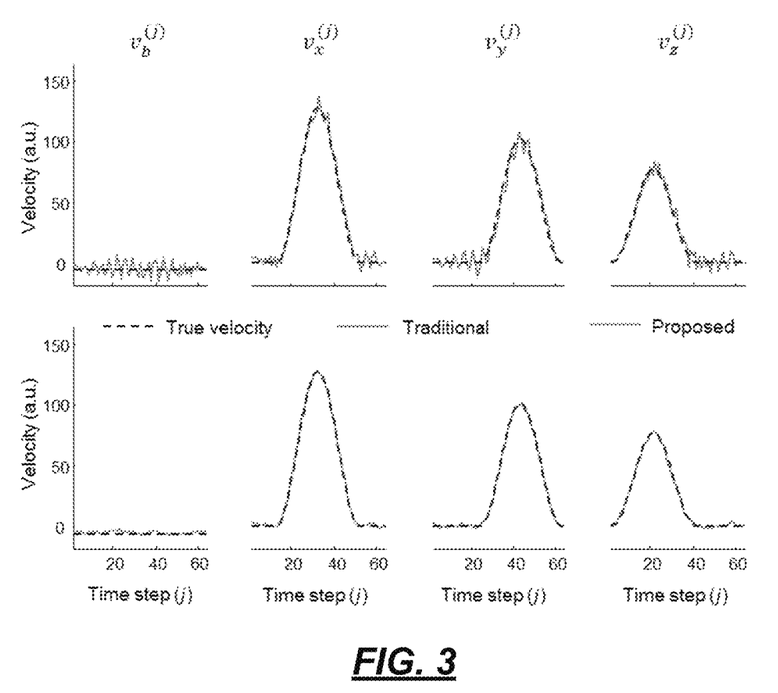
FIG. 3 illustrates a comparison of a conventional reconstruction method and the DiR method of the present disclosure.

The temporal profiles of the four phase components ($\phi_b$, $\phi_x$, $\phi_y$, $\phi_z$) were simulated in Matlab (Mathworks, MA) using Hann functions. Parameters used were: N=64, λ=1×10$^{-10}$, k=1, and c=√2. The measured data ($\vec{\theta}$) were simulation using Equation 9, and white Gaussian noise was added to each measurement to emulate experimental conditions. The reconstructions based on conventional method (Equation 6) and the DiR method of the present disclosure (Equation 12) are shown in FIG. 3. The DiR results were stable and did not vary for a wide range of λ values (1×10$^{-2}$<λ<1×10$^{-14}$). The estimated phases were scaled appropriately to compute the respective velocity.

Thus, as described above, a data processing method, DiR, for phase-based dynamic MRI is presented. Although the method has been described for velocity measurements, it is equally applicable to other phase-based MRI applications, including measurement of tissue stiffness and displacement. The method offers improvement over existing methods in terms of temporal resolution and artifacts.

Adaptive Phase Recovery Method for 4D Phase-Contrast MRI

The direct reconstruction (DiR) method above overcomes some of the limitations of standard sliding window approach. As disclosed above, DiR is based on solving an underdetermined set of equations via regularized least-squares. Being a linear method, DiR treats all velocity components equally, i.e., it assigns equal bandwidth to each component even when the true frequency contents of the components are widely different from each other. Therefore, in DiR, the assigned bandwidth (BWa) for each component cannot exceed ¼th the total bandwidth (BWt), which is determined by the temporal sampling frequency.

To overcome this limitation, in accordance with aspects of the disclosure, an adaptive formulation of DiR, called adaptive DiR (DiRa), is presented. For p=2, bandwidth of each velocity component is adapted based on a current estimate of its temporal frequency contents. This setup allows components with more signal energy in the high-pass region to have higher BWa, leading to improved temporal resolution and reduced artifacts. For 0≤p≤1, DiRa penalizes each component based on the sparsity of that component. The components that are sparser are assigned a larger λ and are penalize stronger.

In the DiR method, for p=2, can be mathematically described in accordance with equation 12 above, where $\hat{\phi}_{DiR}$ is a 4N×1 vector that represents an estimate of the true unknown phase ϕ. In contrast, the DiRa is formulated as:

$$\hat{\vec{\phi}}_{DiRa} = \underset{\lambda_b,\lambda_x,\lambda_y,\lambda_z,\vec{\phi}}{\mathrm{argmin}} \left\| \vec{\theta} - B\vec{\phi} \right\|_2^2 + \lambda_b \left\| R_b \vec{\phi} \right\|_p^p + \lambda_x \left\| R_x \vec{\phi} \right\|_p^p + \lambda_y \left\| R_y \vec{\phi} \right\|_p^p + \lambda_z \left\| R_z \vec{\phi} \right\|_p^p$$
$$\text{s.t. } \frac{1}{\lambda_b^\alpha} + \frac{1}{\lambda_x^\alpha} + \frac{1}{\lambda_y^\alpha} + \frac{1}{\lambda_z^\alpha} = \text{constant} \quad (13)$$

Here, $\lambda_b$, $\lambda_x$, $\lambda_y$, and $\lambda_z$ control the extent of regularization for the background, x, y, and z components of the unknown phase (velocity), respectively, and the linear operator $R_*$ indicates that the regularization is acting only on the "*" component. Matrix R is selected to be a finite difference approximation to the second derivative with respect to time. For 0≤p≤1, other choices of R include, but are not limited to, total-variation and discrete wavelet transform.

Figure 4:
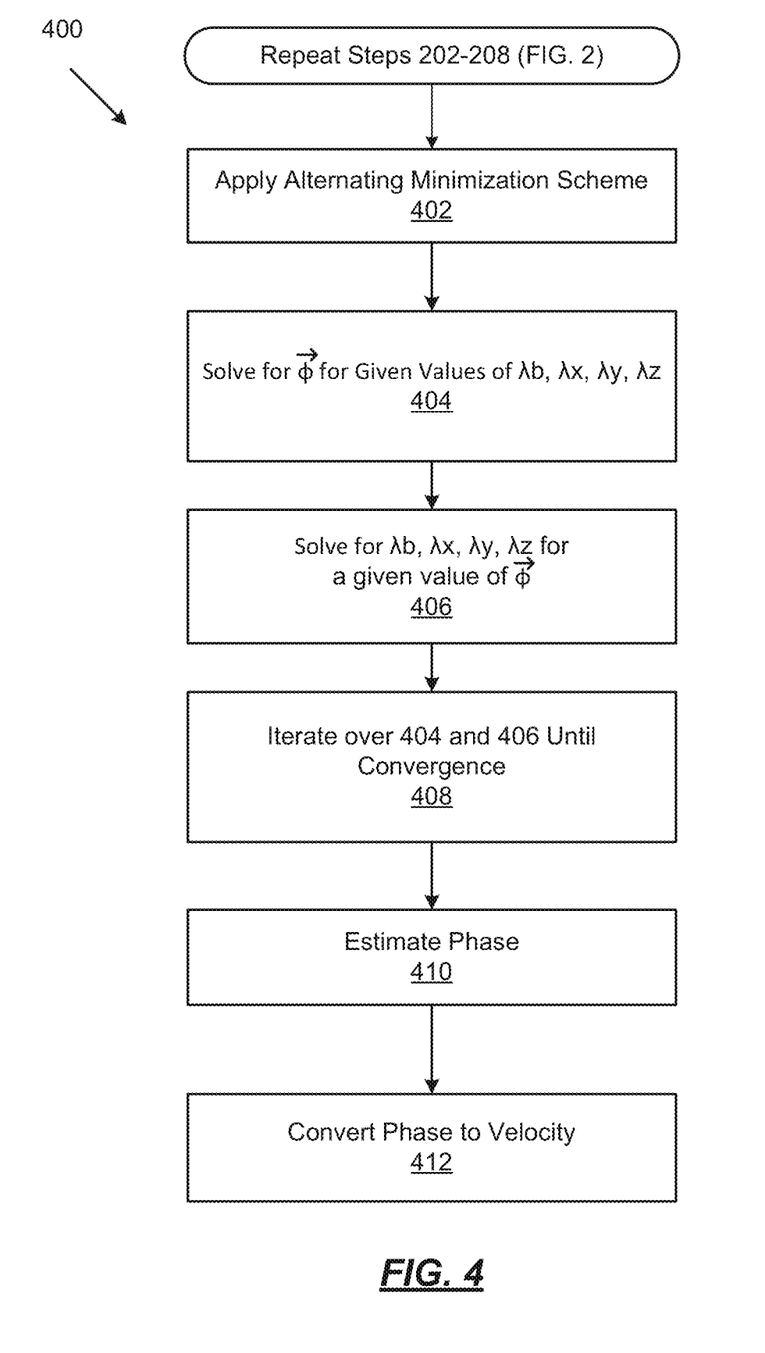
FIG. 4 is an example operational flow in accordance with the present disclosure for implementing an adaptive direct inversion reconstruction (DiRa) of MRI measurements.

With reference to FIG. 4, there is illustrated an operational flow 400 to solve for $\hat{\phi}_{DiRa}$ in Eq. 13. The operational flow begins by repeating the steps at 202-208 in FIG. 2. Next, at 402, an alternating minimization scheme may be used: (i) to solve for ϕ for given values of $\lambda_b$, $\lambda_x$, $\lambda_y$, $\lambda_z$ (closed form at 404 for p=2), (ii) to solve for $\lambda_b$, $\lambda_x$, $\lambda_y$, $\lambda_z$ for a given value of $\vec{\phi}$ (closed form at 406), and (iii) iterate over the last two steps until convergence is reached at 408. Once the phase is estimated at 410, it is scaled at 412 with appropriate values of velocity encoding gradients to yield estimated velocity profiles. In some implementations, both DiR and DiRa operate on reconstructed phase images on pixel-by-pixel basis, and the process (Eq. 12 for DiR and Eq. 13 for DiRa) is repeated for all pixels.

Results

Figure 5:
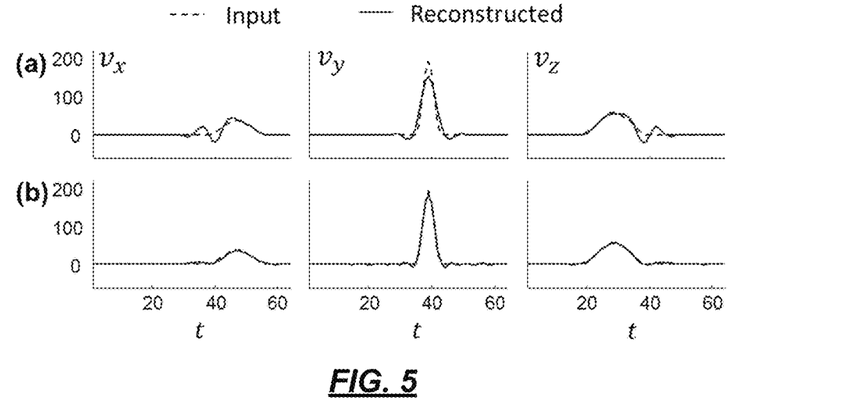
FIG. 5 illustrates example simulation results.
Figure 6:
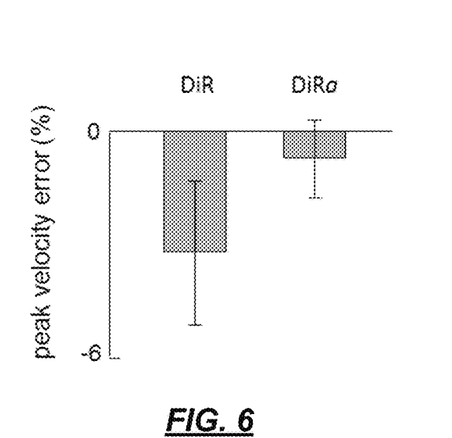
FIG. 6 illustrates a peak velocity error computed as a percentage of a true peak velocity for DiR and DiRa.

Four components of velocity ($v_x$, $v_y$, $v_z$, and $v_b$) were simulated in Matlab using Hann functions. The BFPE data were generated from the simulated velocity profiles. A total of 256 trial runs were considered with different realizations of noise. Also, in each trial run, the widths of the four Hann functions were selected randomly, allowing the components to have different frequency contents. The results from one trial run are shown in FIG. 5. Peak velocity error (computed as a percentage of the true peak velocity) is shown in FIG. 6.

Figure 7:
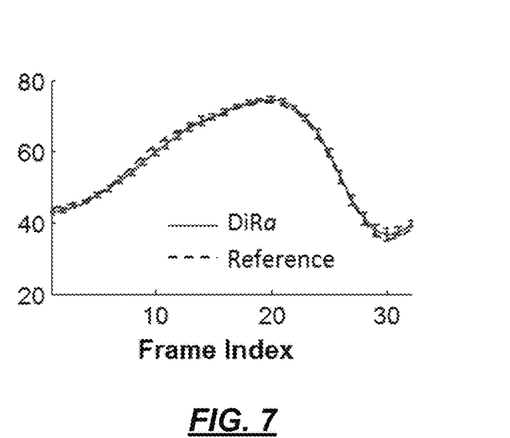
FIG. 7 illustrates example experimental results for DiRa.

Experimental data were collected from a pulsatile home-built phantom using a 1.5 T clinical scanner (Siemens Medical Solutions, Germany) using body matrix receive coils. Six identical datasets were collected using an EPI-PC sequence with BFPE, echo-train-length=7, matrix size=128×96, TE=13.2 ms, TR=23.5 ms, linessegment=7, number of frames=32, parallel acceleration factor=2. For reference standard, GRE-PC sequence was used with referenced four-point encoding, TE=3.28 ms, TR=5.9 ms, lines per segment=1, number of frames=32, and parallel acceleration factor=2. For both EPI-PC and GRE-PC datasets, TGRAPPA with acceleration rate=3 was used for frame-byframe image reconstruction. The DiR and DiRa methods were then applied (for p=2) on the resulting phase images to reconstruct velocity profiles at each pixel from the EPI-PC data. Results are shown in FIG. 7.

Each velocity component in DiR is assigned ¼th of BWt. In practice, different components may have different frequency contents. For example, if the encoding direction is aligned with the flow direction at a given pixel, the signal for that pixel will primarily reside in one of the three spatial components. In this case, it is not reasonable to waste ¼th of BWt on components that have minimum or no signal energy. When considering p=2, background phase may vary slowly over time, i.e., has a small value of $\|R_b\phi\|_2^2$, and may require less than ¼th of BWt for high-fidelity representation.

The adaptive method, DiRa, by independently adjusting the regularization weight on each component, allows unequal distribution of BWt among the components. This setup permits higher BWa to components with larger values of $\|R_*\phi\|_2^2$, i.e., signal energy in the high-pass region. FIG. 5 shows an example where there is a discrepancy in frequency contents of $v_x$, $v_y$, and $v_z$, with $v_y$—due to its narrower temporal footprint and higher amplitude—having higher energy in the high-pass region. The DiR method reduces the temporal resolution of $v_y$ while assigning excessively large BWa to $v_x$ and $v_z$, which is manifested in the form of oscillations. FIG. 6 shows that DiRa exhibits smaller bias and variation in the estimation of peak-velocity. The preliminary results presented in FIG. 7 indicate that DiRa is in strong agreement with reference standard. Quantitative comparisons of DiR and DiRa may be performed with the reference standard in vivo.

Thus, the DiRa processing method improves the reconstruction quality of PC-MRI in terms of artifacts and temporal resolution. This same approach may also be applicable to 7D flow, and other phase-based measurements of dynamic processes, such as DENSE and elastography.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method of recovering time-resolved velocity from a phase-contrast magnetic resonance imaging (MRI) data set, comprising:
    acquiring a MRI data set using a magnetic resonance imaging (MRI) device using a balanced four-point acquisition (BFPA);
    using a processor of a computing device to perform:
        reconstructing a phase encoding matrix (B) based on a velocity encoding sequence used to determine the phase-contrast MRI data set;
        constructing an operator (R) as a regularization operator;
        reading an image phase (θ) along a temporal dimension at a pixel or voxel;
        estimating a velocity phase vector ($\vec{\phi}$) along a temporal dimension using a relationship:

$$\hat{\phi}_{DiRa} = \underset{\lambda_b, \lambda_x, \lambda_y, \lambda_z, \phi}{\operatorname{argmin}} \ \|\theta - B\phi\|_2^2 + \lambda_b \|R_b\phi\|_p^p + \lambda_x \|R_x\phi\|_p^p + \lambda_y \|R_y\phi\|_p^p + \lambda_z \|R_z\phi\|_p^p;$$

scaling the estimated velocity phase vector ($\vec{\phi}$) to a velocity vector profile; and
        generating distortion-free velocity images from the velocity vector profile,
    wherein $\lambda_b$, $\lambda_x$, $\lambda_y$, and $\lambda_z$ control an extent of regularization for background, x, y, and z components of the velocity phase vector ($\vec{\phi}$), respectively,
    wherein $R_b$, $R_x$, $R_y$, and $R_z$ are each linear operators that indicate that the regularization is acting only on the background x, y, and z components of the velocity phase vector ($\vec{\phi}$), respectively, and
    wherein $$\frac{1}{\lambda_b^\alpha} + \frac{1}{\lambda_x^\alpha} + \frac{1}{\lambda_y^\alpha} + \frac{1}{\lambda_z^\alpha} = c,$$

with user defined constant, c, controlling the net regularization strength and α>0 guiding the ratio between $\lambda_b$, $\lambda_x$, $\lambda_y$, and $\lambda_z$ to adaptively adjust regularization strength for each component of $\vec{\phi}$.

2. The method of claim 1, wherein one or more velocity encodings are performed at each time frame and the encoding is varied from frame to frame.

3. The method of claim 2, further comprising using parallel MRI acquisition and acquisition and reconstruction methods to accelerate an MRI data set acquisition process.

4. The method of claim 1, further comprising estimating the velocity phase using a relationship:

$$\hat{\vec{\phi}}_{DiR} = \underset{\phi}{\operatorname{argmin}} \|\vec{\theta} - B\vec{\phi}\|_2^2 + \lambda \|R\vec{\phi}\|_p^p$$

wherein $\vec{\theta}$ represents all N noisy measurements across time, B is a N×4N underdetermined matrix that represents a forward model, R is the regularization operator, $\lambda$ controls an extent of regularization, and $\vec{\phi}_{DiR}$ is a 4N×1 vector that represents an estimate of an unknown phase.

5. The method of claim 1, further comprising estimating the velocity phase vector when p=2 is used to define vector norm.

6. The method of claim 1, further comprising estimating the velocity phase vector for 0≤p≤1 by using iterative methods for sparse signal recovery.

7. The method of claim 1, where $R_b$, $R_x$, $R_y$, and $R_z$ are finite difference operators along time.

8. The method of claim 1, solving for $\hat{\phi}_{DiRa}$ further comprising estimating the velocity phase vector ($\vec{\phi}$) using an alternating minimization scheme to iteratively solve for ($\vec{\phi}$) for given values of $\lambda_b$, $\lambda_x$, $A_y$, $A_z$ and to solve for $\lambda_b$, $\lambda_x$, $\lambda_y$, $\lambda_z$ for a given value of $\vec{\phi}$ until convergence.

9. The method of claim 1, converting the velocity phase vector ($\vec{\phi}$) to velocity vector by scaling the estimated $\vec{\phi}$ using values of velocity encoding gradients to yield estimated velocity profiles.

10. The method of claim 1, wherein the velocity vector recovery is repeated for all pixels or voxels, creating a spatially, temporally resolved velocity vector map.

11. The method of claim 1, wherein the measured phase-contrast MRI data set has two or three spatial dimensions and one temporal dimension.

* * * * *